United States Patent
Bittner (10) Patent No.: US 6,905,838 B1
(45) Date of Patent: Jun. 14, 2005

(54) METHOD AND DEVICE FOR CHARACTERIZING A CULTURE LIQUID

(75) Inventor: Christoph Bittner, Hemel Hempstead (GB)

(73) Assignee: Innovatis AG, Bielefeld (DE)

(*) Notice: Subject to any disclaimer, the term of this patent is extended or adjusted under 35 U.S.C. 154(b) by 329 days.

(21) Appl. No.: 10/088,791

(22) PCT Filed: Oct. 11, 2000

(86) PCT No.: PCT/EP00/10030

§ 371 (c)(1),
(2), (4) Date: Mar. 21, 2002

(87) PCT Pub. No.: WO01/27591

PCT Pub. Date: Apr. 19, 2001

(30) Foreign Application Priority Data

Oct. 11, 1999 (DE) .......................................... 199 49 029

(51) Int. Cl.[7] .............................. C12Q 1/02; C12N 1/00; C12N 13/00
(52) U.S. Cl. ........................ 435/29; 435/173.1; 435/243
(58) Field of Search ................................. 435/173.1, 29, 435/243

(56) References Cited

U.S. PATENT DOCUMENTS

| 4,471,056 A | 9/1984 | Grumet |
| 5,270,173 A | 12/1993 | Yonemori |
| 5,403,735 A | 4/1995 | Maruhashi |
| 5,784,162 A | * 7/1998 | Cabib et al. ................. 356/456 |
| 6,438,396 B1 | * 8/2002 | Cook et al. .................. 600/310 |

FOREIGN PATENT DOCUMENTS

| DE | 3446908 C2 | 7/1985 |
| DE | 3922358 A1 | 1/1991 |
| DE | 4032002 A1 | 6/1991 |
| EP | 0277789 A2 | 8/1988 |
| WO | WO 87/04247 A1 | 7/1987 |

OTHER PUBLICATIONS

Bittner et al. "In situ microscopy for on–line determination of biomass" Biotech. Bioeng. (Oct. 1998) 60(1): 24–35.*
Korber et al. "Bacterial plamolysis as a physical indicator of viability" Appl. Environ. Microbiol. (Nov. 1996) 62(11): 3939–3847.*
Copy of Search results from German priority patent application (in German).

* cited by examiner

Primary Examiner—Jean C. Witz
Assistant Examiner—Susan Hanley
(74) Attorney, Agent, or Firm—Technoprop Colton LLC (57) ABSTRACT

In a method for characterizing a culture liquid, in particular in a bioreactor, by illuminating the cells (22) contained in the culture liquid the culture liquid is analyzed in situ, microscopic imaging of the cells (22) and by evaluating the image. The illumination is carried out as dark-field illumination, and the image evaluation comprises a comparison of the intensities of the light output by the interior of the cell and by the edge of the cell, by means of which comparison living and dead cells (22) are distinguished in order to determine the vitality of the culture liquid.

9 Claims, 6 Drawing Sheets

METHOD AND DEVICE FOR CHARACTERIZING A CULTURE LIQUID

The invention relates to a method in accordance with the preamble of patent claim 1, and to an apparatus for carrying out the method.

As is shown, for example, in DE 40 32 002 C2, such a method is used in closed containers and systems in which microorganisms are cultivated under sterile conditions. Automatic control of the cultivation process requires measured values that indicate the state of the culture liquid, in particular the cell concentration. However, control functions satisfactorily only when these values are measured quickly, that is to say on-line. All off-line methods such as, for example, manual sampling and analysis are useless for this purpose. Again, the addition of analytical reagents to the reactor contents is usually not permitted.

Consequently, optical detectors are readily used for measuring the light absorption, light scattering or the fluorescence of the cells. Unfortunately, as a rule these methods do not distinguish between the cells and the liquid surrounding them. It is therefore difficult to obtain detailed statements on the cell population in the closed bioreactor.

The method and the apparatus in accordance with DE 40 32 002 C2 therefore constitute a substantial advance. In the case of this method, the cells are illuminated and imaged by a microscope and a video camera, and this image is analyzed by means of electronic image processing. There is no need to remove the cells. The microscoped volume is defined optically or mechanically, similar to a counting chamber. Cells can be detected selectively by the image processing, and their concentration, size and morphology can be determined. The solution in which the cells float, concomitants, contaminations and air bubbles can be distinguished reliably from the cells. The in-situ microscopy supplies as measured values the cell concentration and cell size distribution. The dry biomass can be determined from these two.

However, it is also desired to determine the vitality of the culture liquid. The vitality of a cell sample is defined as the ratio of the living cells divided by the total number of the cells (some of the living and dead cells). The vitality is an important parameter for culturings on an industrial scale. In these processes, the biomass is used repeatedly until the dead cell fraction is so high that a new cell culture must be used. Another purpose of use is the inoculation of culturings: if the vitality of a cell sample and the cell concentration are known, the required volume for inoculating a culture can be calculated (for example when adding yeast in breweries). It would therefore be a great advance if the absolute cell concentration and the vitality can be determined with the aid of the same sample. However, it has not so far been possible to detect the cell vitality as an additional parameter for each cell individually.

It is therefore the object of the invention to indicate a method with the aid of which in the case of in-situ microscopic observation of cells in the bioreactor it is possible to assess the vitality of the individual cells directly, and to create an apparatus for carrying out the method.

In the method according to the invention, the illumination of the cells is carried out as dark-field illumination. In this illuminating arrangement, no direct light from the illuminating light source participates in the imaging, but only the light output by the illuminated cells, that is to say scattered light, for example. When evaluating the image, a comparison of the intensities of the light output by the interior of the cell and by the edge of the cell is carried out. It is thereby possible to distinguish living and dead cells such that the vitality of the culture liquid can be determined.

The method uses the property of cells to deflect light. A living cell directs the light substantially in the forward direction, while a dead cell deflects the light diffusely to all sides. If use is made of an optical arrangement for angle-selective detection of the light deflected by the cells, that is to say a dark-field arrangement, and if the latter is built into an in-situ microscope, it is possible to detect the cell vitality directly in the reactor.

The invention is explained in more detail below with the aid of the drawings, in which.

Figure 1:
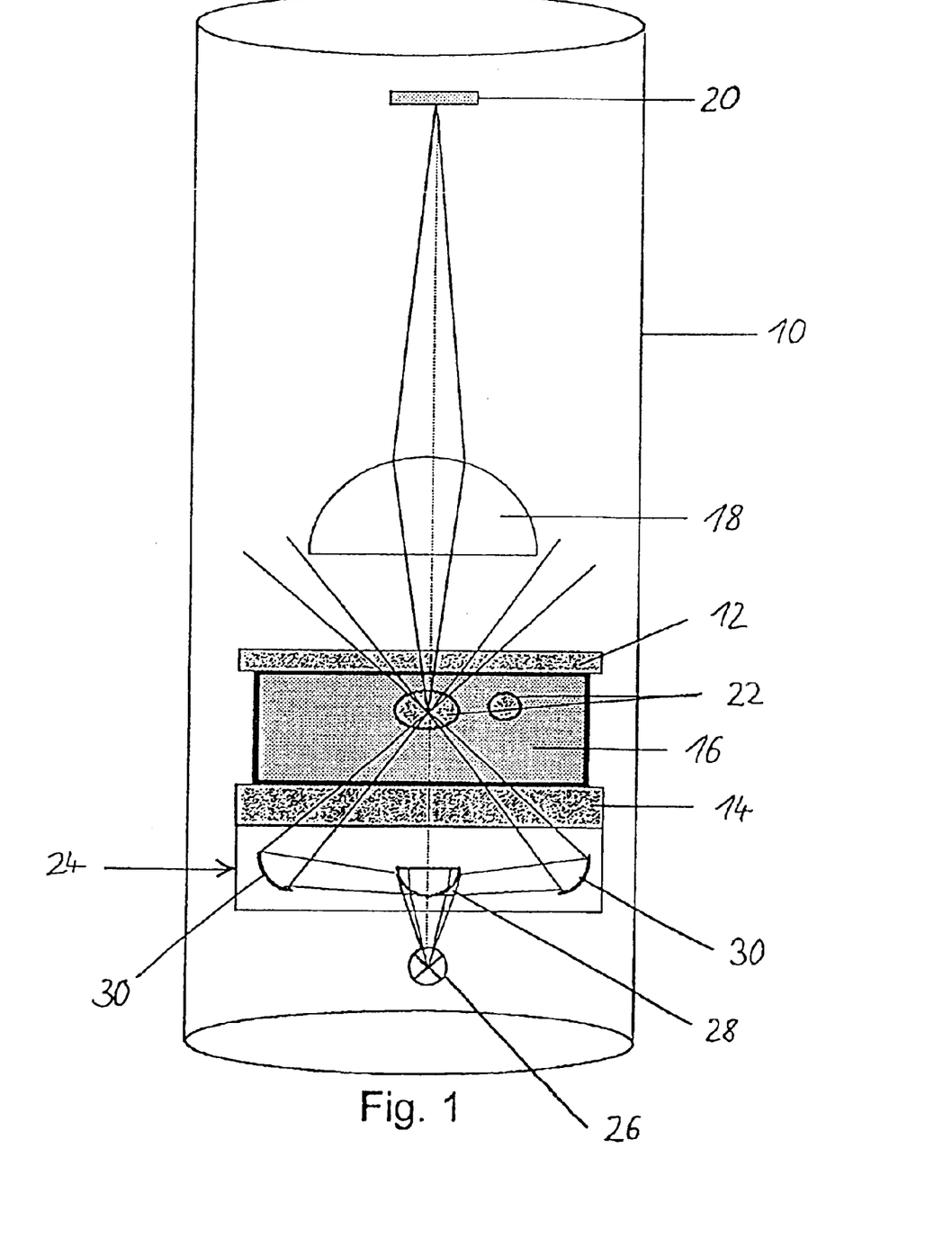
FIG. 1 shows a schematic of a first embodiment of the apparatus according to the invention.

The apparatus shown in FIG. 1 comprises a cylindrical tube 10 that is immersed in the culture liquid in the bioreactor (not illustrated). Located inside the tube are two glass plates 12, 14 arranged in parallel and at right angles to the tube axis. The interspace between the glass plates 12, 14 forms a sample volume 16 of the culture liquid to be investigated. In order for the culture liquid to be able to flow freely through the sample volume 16, the openings (not illustrated) are arranged situated opposite in the wall of the tube 10 in the region of the sample volume 16. Since it is advantageous to immobilize the liquid in the sample volume 16 during the investigation, the openings are to be sealed when required. Moreover, one of the glass plates 14 can be shifted along the tube axis such that the thickness of the sample volume 16 can be varied.

Arranged outside the sample volume 16 is a microscope objective 18 whose optical axis coincides with the tube axis. Arranged on the side of the objective 18 opposite the glass plates 12, 14 is an electronic image recorder whose pickup surface is at right angles to the optical axis of the objective 18. The distances of the objective 18 from the glass plate 14, and of the image recorder 34 from the objective 18, are selected in accordance with the focal length of the objective 18 such that an object, that is to say, in particular, a cell 22 to be investigated, can be sharply imaged inside the sample volume 16 on the pickup surface of the image recorder 20.

Located on the side of the glass plates 12, 14 opposite the objective 18 and the image recorder 20 is a dark-field condenser 24 with a substantially punctiform light source 28, a convex mirror 28 arranged on the optical axis of the objective 18, and a concave mirror 30 that is arranged in a radially symmetric fashion and approximately annularly about the optical axis, and is illustrated only partially in FIG. 1. The dark-field condenser 24 shown in FIG. 1 is what is known as a cardioid condenser. The light of the light source 26 is reflected by the convex mirror 28 onto the concave mirror 30, which reflects it as a weakly convergent rotationally symmetrical beam obliquely to the optical axis of the objective 18 into the sample volume 16. The light beams emerging from the concave mirror 30 therefore cross one another inside the sample volume 16 and strike cells 22 inside the sample volume, which are illuminated thereby.

The mode of operation of the arrangement in FIG. 1 is described below. In order to immobilize the culture liquid inside the sample volume 16, the openings in the wall of the tube 10 are sealed such that the flow is interrupted. Subsequently, the displaceable glass plate 14 is moved in the direction of the fixed glass plate 12 until the interspace between the two glass plates 12, 14 is so small that the sample volume 16 is formed only by a thin liquid layer. The thickness of this layer should correspond to the depth of field of the objective 18 such that all the cells 22 inside the sample volume 16 can be sharply imaged.

The light of the dark-field condenser 24 strikes the cells 22, but does not pass directly into the objective 18, since the latter is arranged outside the beam path of the dark-field condenser 24. Consequently, it is only the light output by the illuminated cells 22 that passes into the objective 18, and it produces a sharp image of the cells 22 on the light-sensitive pickup surface of the image recorder 20. This image is digitized and analyzed by image processing software.

In order to distinguish between living and dead cells 22, the fact is utilized that in the case of the imaging described here by means of dark-field illumination, the interior of living cells appears substantially darker than the edge of the cells, while in the case of dead cells the interior of the cell appears approximately as bright as the edge. It follows that the assessment of the vitality of the culture liquid can be undertaken in a simple way by means of the image processing by comparing the brightness of the edge of the cell with that of the cell interior in the case of individual cells, deciding on this basis whether a living or a dead cell is involved, and subsequently determining the fraction of living cells in the total number of cells.

It is possible to dispense with immobilizing the culture liquid in the sample volume 16 by sealing the openings if the cells 22 are illuminated only briefly during the exposure time of the image recorder (approximately ⅟₅₀ sec), such that a sharp image can be produced despite the movement of the cells 22. This brief illumination is achieved by a pulsed operation of the light source 26. Flash lamps, LEDs and lasers are suitable, for example, as light source 26.

Figure 2:
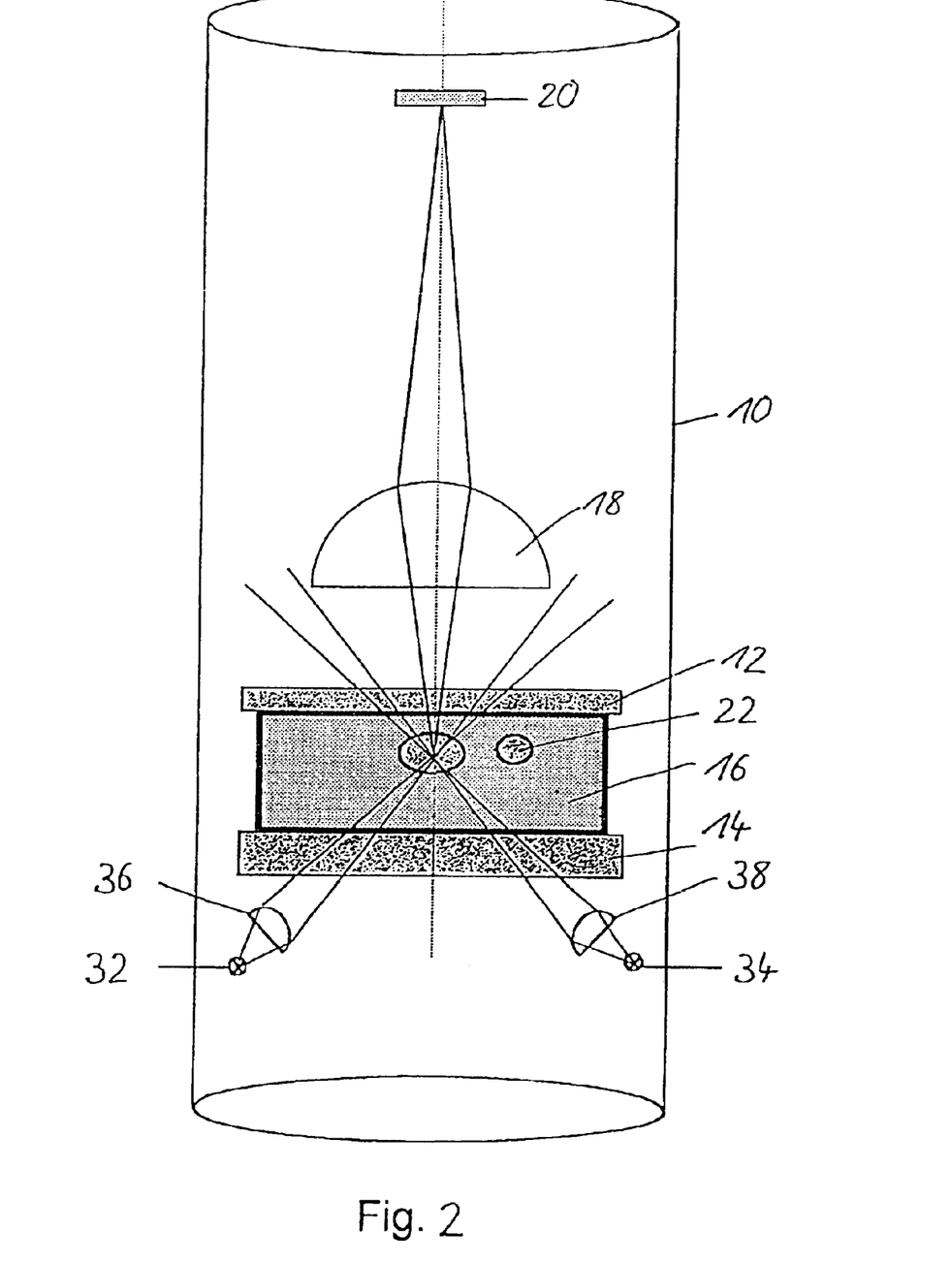
FIG. 2 shows a second embodiment with a modified illuminating arrangement.

FIG. 2 shows a second embodiment similar to the arrangement of FIG. 1, which comprises a dark-field condenser with a number of punctiform light sources 32, 34, of which two opposite light sources are shown by way of example in FIG. 2. These light sources 32, 34 are arranged in a coronal and rotationally symmetric fashion about the optical axis. Their light is focused by lenses 36, 38, whose optical axes cross one another at a point inside the sample volume 16, into the sample volume 16 such that a beam path is produced that corresponds to that of the cardiolid condenser 18 of FIG. 1.

Figure 3:
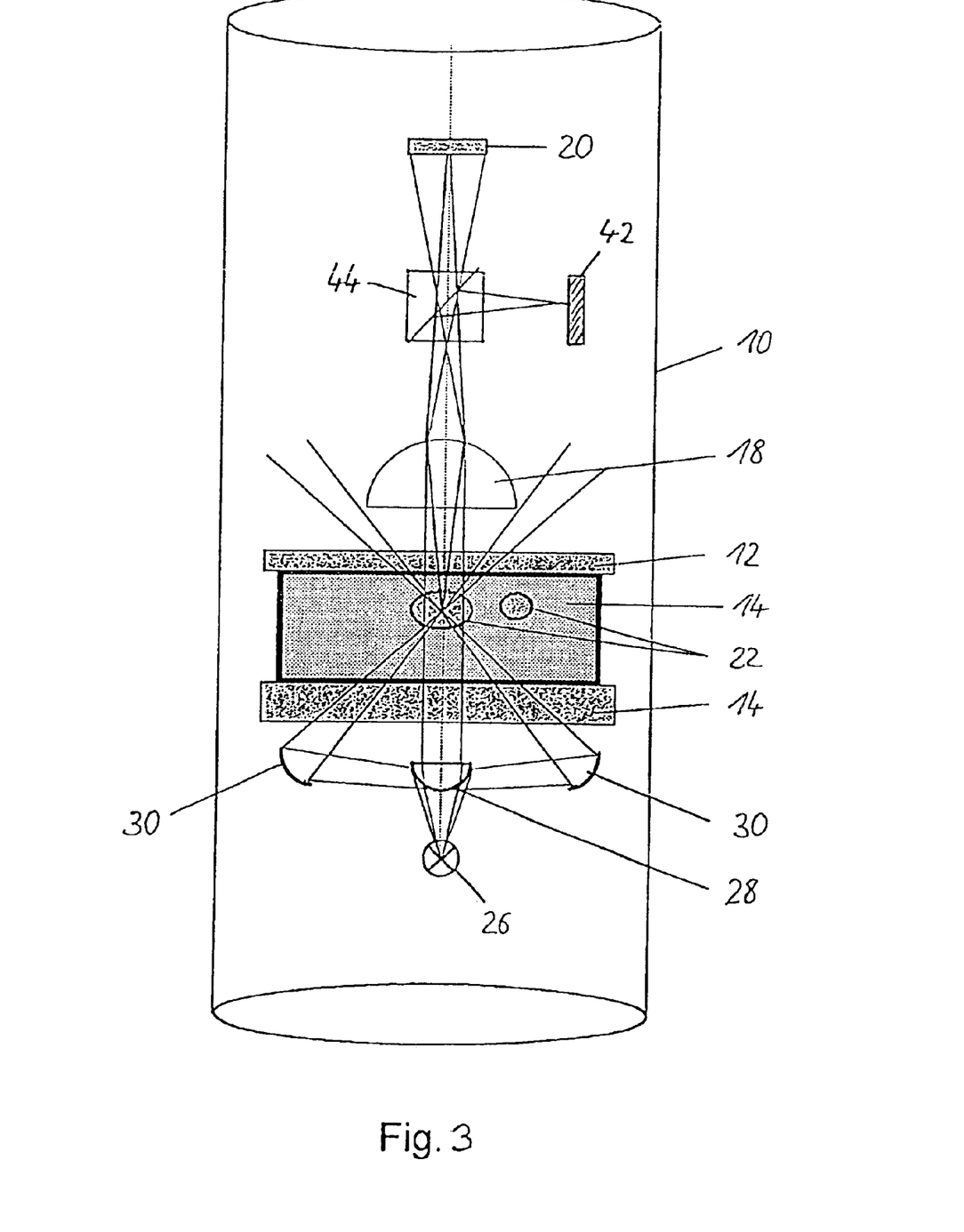
FIG. 3 shows an embodiment that is provided for bright-field microscopy in addition to dark-field microscopy.

FIG. 3 shows a further embodiment of the apparatus according to the invention, which also permits light-field microscopy to be carried out simultaneously apart from the dark-field microscopy. For this purpose, the arrangement is provided with a condenser 24 that has an arrangement with an approximately punctiform light source 26, a convex mirror 28 and a concave mirror 30 that is arranged annularly around the optical axis of the microscope objective 18 and corresponds to the cardioid condenser 24 of FIG. 1 and which permits the dark-field illumination described there of the sample volume 16. By contrast with the condenser 24 of FIG. 1, however, the convex mirror 28 is designed such that it reflects a portion of the light emanating from the light source 26 to the concave mirror 30, but passes the remaining fraction of the light. This transmitted fraction transilluminates the sample volume 16 such that the fraction passed by the culture liquid and the cells 22 can enter the objective 18 and produce an image on the image recorder 20. Thus, a total of two images are produced: on the one hand, by the dark-field illumination of the cells 22 and imaging of the illuminated cells and, on the other hand, a transmission imaging of the light of the bright-field illumination transmitted by the cells 22. For the purpose of separating the two images, a beam splitter cube that reflects a fraction of the light entering the beam splitter 44 in a direction perpendicular to the optical axis is arranged on the optical axis between the microscope objective 18 and the image recorder 20. This light strikes a second image recorder 42, which is provided in the same way as the first image recorder 20 for the purpose of producing and digitally processing an image.

The image processing requires these two images to be separated optically from one another. This is performed by polarizing the light used for the two types of illumination, that is to say for the dark-field illumination and the bright-field illumination, differently and once again separating the light entering the microscope objective 18 from the sample volume 16 in accordance with the different directions of polarization in the imaging beam path by means of the polarizing beam splitter 44 such that the light passed by the beam splitter 44 corresponds to a first direction of polarization and the light reflected by the beam splitter 44 corresponds to the direction of polarization at right angles thereto. The polarization coding of the light used for the different illuminations is performed by a polarizing coating of the convex mirror 28 which has the effect that light reflected by the convex mirror 24 for the purpose of dark-field illumination in a first direction, that is to say at right angles to the plane of the drawing, for example, is polarized such that the light output by the cells 22 on the basis of the dark-field illumination into the microscope objective 18 likewise corresponds to this direction of polarization. The beam splitter 44 is arranged such that it reflects the light of this direction of polarization and produces on the second image recorder 42 an image originating from the dark-field illumination. By contrast, light passed by the convex mirror 28 is polarized at right angles to the reflected light such that the light transmitted by the cells 22 and entering the microscope objective 18 is likewise polarized in this direction and likewise passed by the beam splitter 44 such that an image that corresponds to the bright-field illumination is produced on the first image recorder 20.

In a comparable way, the light used for the dark-field illumination and the bright-field illumination can be color coded such that the light used for the dark-field illumination has a different wavelength to the transmitted light of the bright-field illumination. This permits a simple distinction between the images, produced by the various types of illumination, by means of corresponding color filters that are to be positioned (in a way not shown) in front of the respective image recorders 20, 42.

It is also possible to dispense with the second image recorder 42 and the beam splitter 44 such that both images are produced on a single image recorder 20. The quality of a digital image recorder that the individual pixels of the image recorder are respectively sensitive only to one color (red, green or blue) is utilized in this case. The images of different colors can now be separated by reading out the color-sensitive pixels of one color in each case and combining them to form an image.

A very simple type of color coding consists in providing a light source 26 of wide spectral band and coating the convex mirror 28 dichroically such that it reflects light of one wavelength and passes light of another wavelength.

Furthermore, it is possible to provide different monochromatic light sources such as, for example, LEDs or lasers for the two illuminating beam paths.

Figure 4:
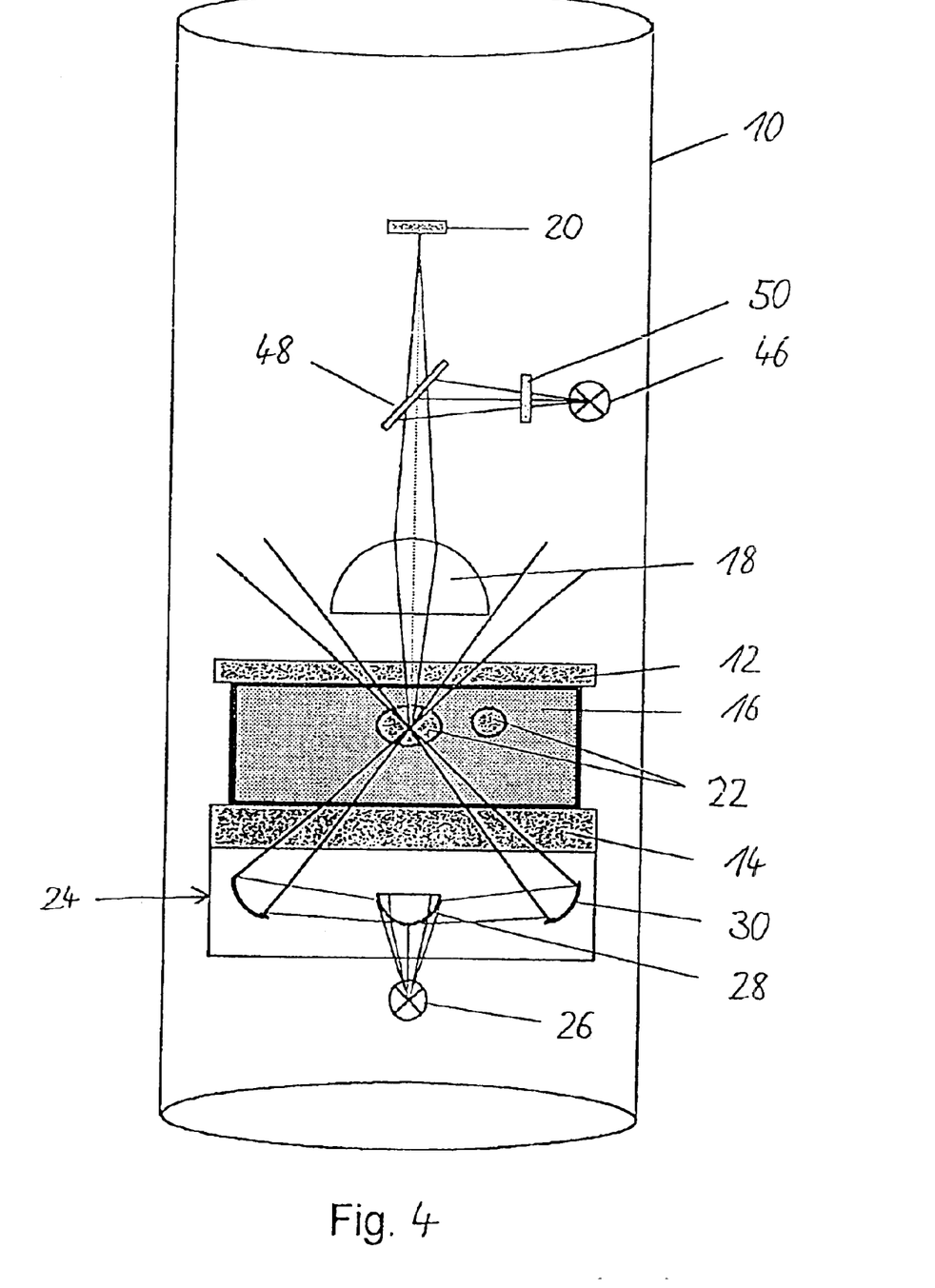
FIG. 4 shows an embodiment that is provided for fluorescence microscopy in addition to dark-field microscopy.

The arrangement shown in FIG. 4 is also suitable for carrying out fluorescence microscopy apart from dark-field microscopy. The arrangement is provided, on the one hand, with the dark-field condenser 24 known from FIG. 1. Provided in addition in the tube region opposite the dark-field condenser 24 is a further light source 46 that is offset by comparison with the optical axis of the microscope objective 18, and whose light is reflected by a beam splitter 48 by 90 degrees in the direction of the microscope objective 18 and focused by the latter into the sample volume 16. Arranged between the fluorescent light source 46 and the beam splitter 48 is a filter 50 that spectrally constricts the excitation light emanating from the fluorescent light source 46. The excitation light excites the cells 22 in the sample volume 16 to fluoresce, and the output fluorescent light passes in the reverse direction through the microscope objective 18 and strikes the beam splitter 48. The beam splitter 48 is designed such that, by contrast with the excitation light, it passes the fluorescent light shifted spectrally to higher wavelengths, and permits imaging by fluorescent light on the image recorder 20. As a result, two different images are produced on the image recorder 20, specifically the image produced by the dark-field illumination in the usual way, and an image of the fluorescent light. The separation of the dark-field and fluorescent images is performed by the already described separation of the separations of the image recorder 20, that is to say by separation of the data of pixels with different color sensitivity. A further possibility consists in the temporal separation of the images by alternately pulsing in rapid sequence the light source 26 of the dark-field condenser 24 and the fluorescent light source 46, and reading out the images on the image recorder 20 in a temporally separated fashion.

Figure 5:
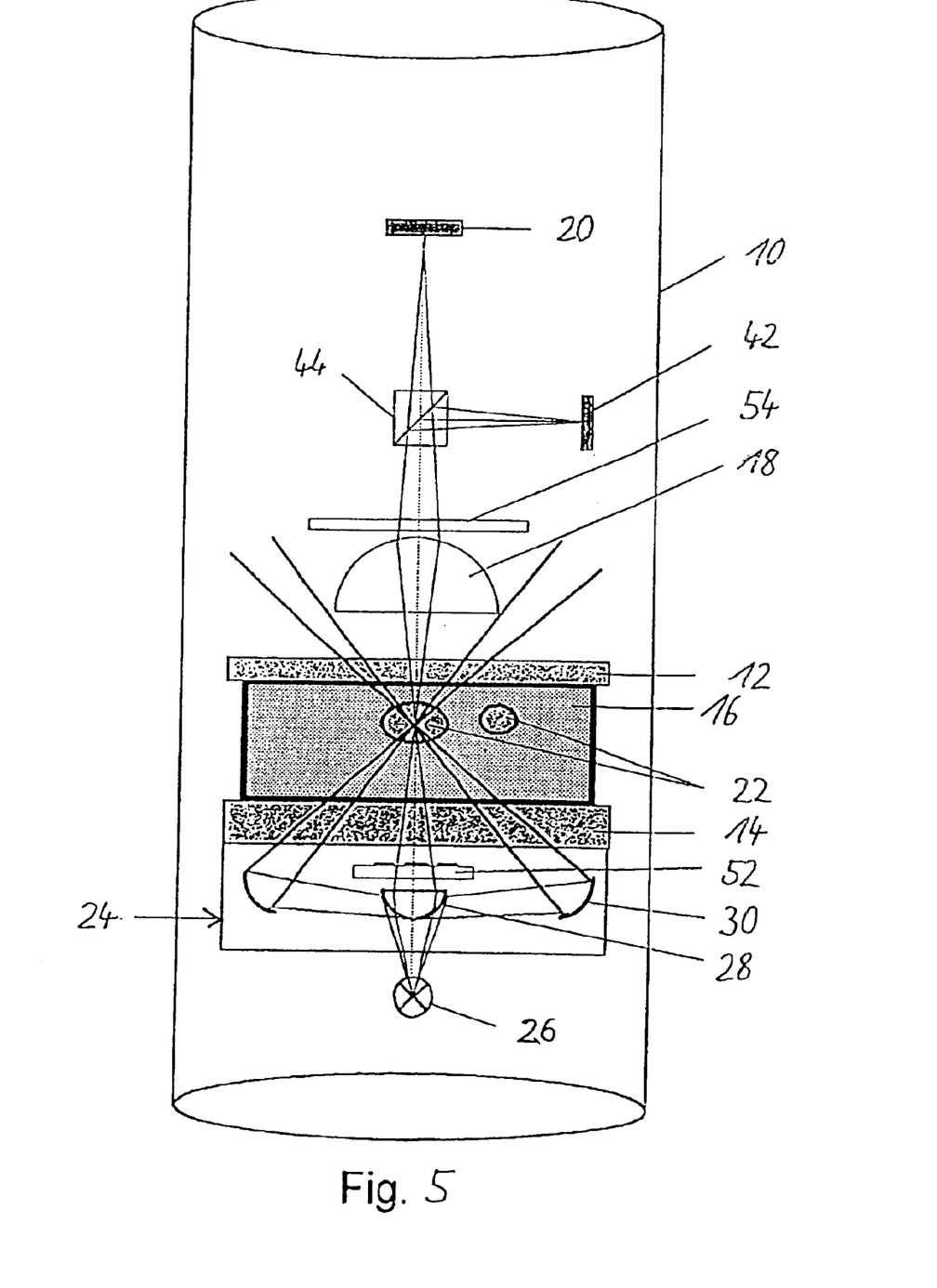
FIG. 5 shows an embodiment that is provided for phase contrast microscopy in addition to dark-field microscopy.

FIG. 5 shows an arrangement that is suitable simultaneously for phase contrast microscopy apart from dark-field microscopy. The arrangement shown corresponds substantially to FIG. 3. The convex mirror 26 of the dark-field condenser 24 is coated so as to polarize such that it reflects light of one direction of polarization and transmits light of the direction of polarization at right angles thereto, and so dark-field illumination and bright-field illumination of the sample volume 16 are carried out simultaneously. As in FIG. 3, there is provided in the imaging beam path a beam splitter 44 that reflects light of one direction of polarization and transmits the light of the direction of polarization at right angles thereto such that an image of the transmitted light can be produced on an image recorder 20 arranged on the optical axis of the microscope objective 18, and an image of the reflected light can be produced on a further image recorder 42 in the direction of reflection. In this way, the images that are produced by the different types of illumination can be distinguished by means of the polarization, as is described adequately in conjunction with FIG. 3.

By contrast with FIG. 3, an arrangement for phase contrast microscopy is arranged in the bright-field beam path. Said arrangement comprises an annular diaphragm 52 arranged directly behind the convex mirror, and a phase plate 54 arranged between the microscope objective 18 and the beam splitter 44. The annular diaphragm 52 and the phase plate 54 are at right angles to the optical axis of the microscope objective 18. The light of the light source 26 transmitted by the convex mirror 28 firstly passes the annular diaphragm 52 and, after it has passed the sample volume 16, enters the microscope objective 18 where it is focused onto the first image recorder 20 through the phase plate 54 and the beam splitter 44. This phase contrast arrangement known per se produces an image of higher contrast than in the case of the simple bright-field illumination arrangement shown in FIG. 3.

Figure 6:
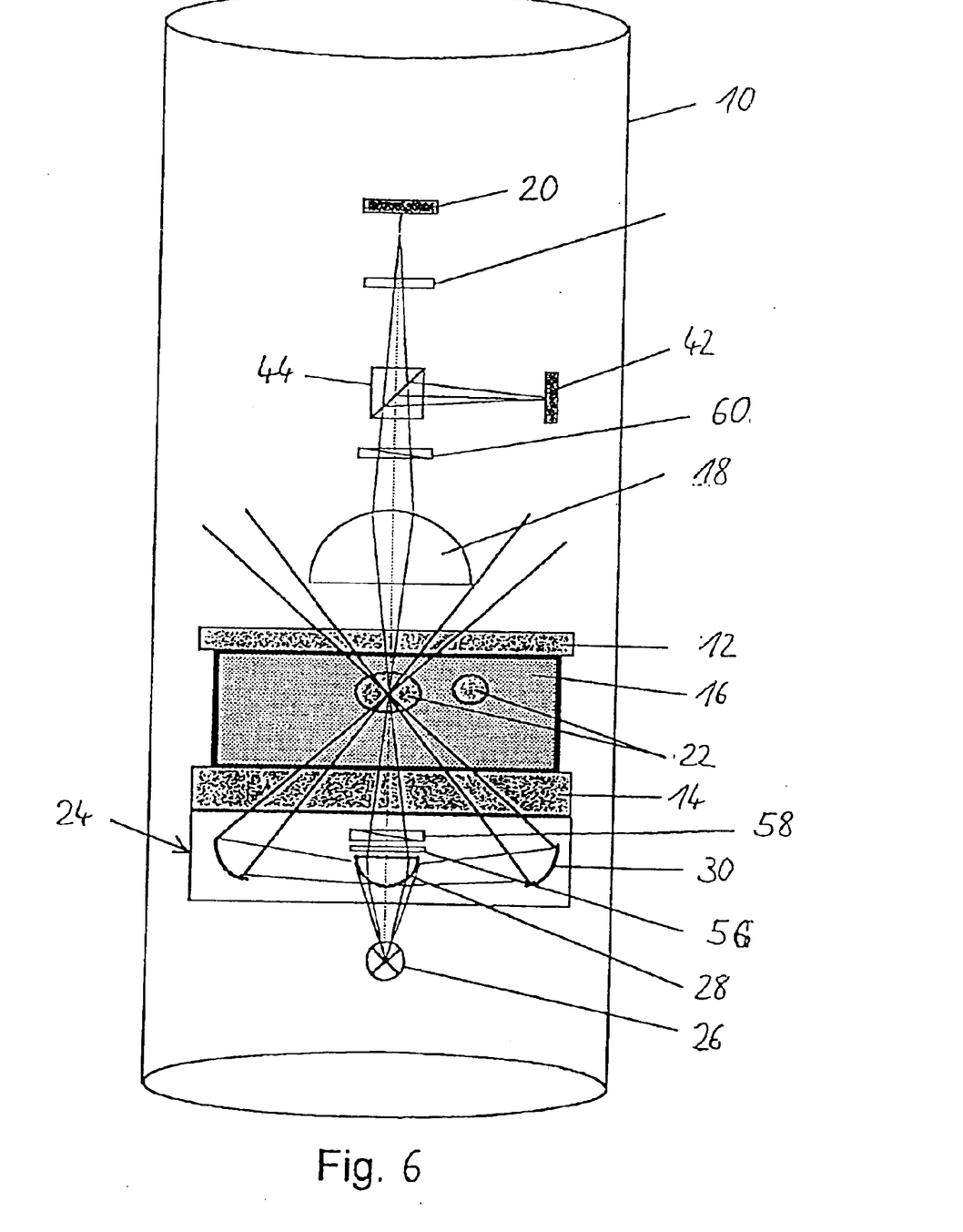
FIG. 6 shows an embodiment that is provided for interference contrast microscopy in addition to dark-field microscopy.

The arrangement shown in FIG. 6 is also provided for interference contrast microscopy in addition to dark-field microscopy. This design corresponds substantially to the arrangement, shown in FIG. 5, for phase contrast microscopy, but in FIG. 6 the annular diaphragm 52 is replaced by a λ/4 plate 56 and a Wollaston prism 58 arranged therebehind, and instead of the phase plate 54 of FIG. 5 use is made of a second Wollaston prism 60 in the imaging beam path between the microscope objective 18 and the beam splitter 44. Moreover, an additional analyzer 62 is inserted in the transmission beam path between the beam splitter 44 and the first image recorder 20.

The convex mirror 28 is coated in a known way so as to polarize such that the light transmitted by the convex mirror 28 is polarized. This light passes the λ/4 plate 56 and the first Wollaston prism 58, which splits each individual light beam into two beams of different polarity that fall into the sample volume 16. If the beams strike an object there such as, for example, a cell 22, the object can cause a path difference between the different light beams. The beams passing the sample volume 16 are focused by the microscope objective 18 and impinge on the second Wollaston prism 60, which unites the two beams again. These beams impinge through the beam splitter 44 on the first image recorder 20 and produce an interference contrast image there. As a result of the path difference that is produced by the objects in the sample volume 16, an image of very high contrast is produced, it being possible to vary the contrast by displacing the second Wollaston prism 60 along the optical axis of the microscope objective the optical axis of the microscope objective 18.

As in the case of the arrangements already discussed, apart from interference contrast imaging it is possible to produce an image of the light beams reflected by the beam splitter 44 on the second image recorder 42, which image originates in a known manner from the dark-field illumination.

What is claimed is:

1. A method for characterizing the vitality of a culture liquid in a bioreactor comprising the steps of:
    a) illuminating cells contained in the culture liquid by dark-field illumination;
    b) analyzing the culture liquid in situ by microscopic imaging of said cells, wherein the microscopic imaging produces an image of said cells;
    c) evaluating the image of said cells by comparing the intensities of the light scattered by the interiors of the cells to the light scattered by the edges of the cells by said dark-field illumination, wherein
        i) the interiors of living cells appear darker compared to the edges of said cells, and
        ii) the interiors of dead cells appears approximately as bright as the edges of said cells; and
    d) comparing of the number of living cells to the number of dead cells to determine the vitality of the culture liquid.

2. The method of claim 1, further comprising carrying out a bright-field illumination of the cells during said dark-field illumination, wherein the step of evaluating the image of the cells further comprises observing the bight-field illumination scattered by said cells.

3. The method of claim 1, further comprising fluorescently illuminating the cells during said dark-field illumination, wherein the step of evaluating the image of the cells comprises observing the fluorescent light scattered by said cells.

4. The method of claim 1, further comprising carrying out an interference contrast observation of the cells during said dark-field illumination, wherein the step of evaluating the image of the cells further comprises observing contrast produced by said cells.

5. The method of claim 1, further comprising the steps of carrying out a bright-field illumination with phase contrast of the cells during said dark-field illumination, wherein the step of evaluating the image of the cells comprises observing the phase contrast produced by said cells.

6. The method as claimed in claim 2, wherein the polarizations of the light used for the dark-field and light-field illuminations are different and the images that are produced by the dark-field and the light-field illuminations are distinguished by the different polarizations of the light that produce said images.

7. The method as claimed in claim 2, wherein the wavelengths of the light used for the dark-field and light-field illuminations are different and that the images produced by said dark-field and said light-field illuminations are distinguished by the different wavelengths of the light that produce said images.

8. The method as claimed in claim 1, wherein the illumination is carried out with pulsed light.

9. The method of claim 1, wherein the sample of said liquid culture to be imaged is temporarily immobilized during the image evaluation step.

* * * * *